(12) United States Patent
Alters et al.

(10) Patent No.: US 6,753,135 B2
(45) Date of Patent: Jun. 22, 2004

(54) BIOLOGICAL MARKERS FOR EVALUATING THERAPEUTIC TREATMENT OF INFLAMMATORY AND AUTOIMMUNE DISORDERS

(75) Inventors: Susan E. Alters, Palo Alto, CA (US); Karen L. Cheal, Mountain View, CA (US); Aaron B. Kantor, San Carlos, CA (US)

(73) Assignee: SurroMed, Inc., Menlo Park, CA (US)

( * ) Notice: Subject to any disclaimer, the term of this patent is extended or adjusted under 35 U.S.C. 154(b) by 106 days.

(21) Appl. No.: 09/956,757

(22) Filed: Sep. 20, 2001

(65) Prior Publication Data

US 2002/0072484 A1 Jun. 13, 2002

Related U.S. Application Data

(60) Provisional application No. 60/234,313, filed on Sep. 20, 2000, provisional application No. 60/239,281, filed on Oct. 10, 2000, provisional application No. 60/246,137, filed on Nov. 6, 2000, and provisional application No. 60/304,563, filed on Jul. 10, 2001.

(51) Int. Cl.$^7$ .............................................. C12Q 1/00
(52) U.S. Cl. ............................................................. 435/4
(58) Field of Search ................................................ 435/4

(56) References Cited

U.S. PATENT DOCUMENTS

| | | |
|---|---|---|
| 5,683,983 A | 11/1997 | Barrett et al. |
| 5,874,080 A | 2/1999 | Hebert et al. |
| 5,908,839 A | 6/1999 | Levitt et al. |

OTHER PUBLICATIONS

U.S. patent application Ser. No. 09/558,909, Ringold et al., filed Apr. 26, 2000.
Boumpas et al. (1991) *Clinical and Experimental Rheumatology* 9:413–423.
DiBattista et al. (1991) *J. Clin. Endocrinol. Metab.*, 72: 316–326.
Fauci et al. (1974) *J. Clin. Invest.* 53:240–246.
Gemou–Engesaeth et al. (1994) *Pediatr Allergy Immunol.* 5:170–177.
Gemou–Engesaeth et al. (1997) *Pediatrics*, 99: 695–703.
Jensen et al. (1998) *Biochem J.*, 334:489–503.
Kestens et al. (1994) *Clin. Exp. Immunol.* 95:436–441.
Keyszer et al. (1999) *J. Rheumatol.* 26:251–258.
Li et al. (1999) *Am J. Physiol.* 276:G1425–G1434.
Liu et al. (2001) *J. Allergy Clin. Immunol.* 108:29–38.
Marhaug et al. (1994) *Baillieres Clin. Rheumatol* 8:553–573.
Morin et al. (1999) *J Pharmacol Exp Ther.* 289:1634–1640.
Oehling et al. (1997) *Allergy*, 52:144–154.
Read et al. (1998) *Eur. J. Immunol.* 28:3435–3447.
Sharif et al. (1998) *Arthritis Rheum.* 41:1203–9.
Tedder et al. (1995) *FASEB J.*, 9:866–873.
Vincenti et al. (1996) *Critiial Rview in Eukaryotic Gene Expression* 6(4):391–411.
Vukmanovic et al. (1992) *Clin. Immunol. Immunopathol.*, 65:261–270.
Wolf et al. (1996) *Clin. Exp. Immunol.*, 105:537–543.
Dau et al. (Feb. 1994) *Clin Immunology and Immunopthology* 70(2):159–165.
Jovanovic et al. (1977) *J. Rheumatology* 24(5):916–925.

*Primary Examiner*—Patrick J. Nolan
(74) *Attorney, Agent, or Firm*—Swanson & Bratschun LLC

(57) ABSTRACT

Novel biological markers indicative of the action of an anti-inflammatory or immunosuppressive drug can be used to evaluate drug efficacy and compare local and systemic drug effects. They can also aid in comparison of different drugs, doses, and delivery routes. The biological markers include cell populations, cell surface antigen expression levels, and soluble factor concentrations. Measurement values of the novel biomarkers were shown to change significantly in allergic, atopic asthmatic, and healthy subjects after administration of prednisone.

13 Claims, 1 Drawing Sheet

BIOLOGICAL MARKERS FOR EVALUATING THERAPEUTIC TREATMENT OF INFLAMMATORY AND AUTOIMMUNE DISORDERS

RELATED APPLICATIONS

This application claims the benefit of U.S. Provisional Application No. 60/234,313, "Identification of Biomarkers in Atopic Asthma: Effects of Glucocorticoids on Cell Surface and Soluble Factors," filed Sep. 20, 2000; U.S. Provisional Application No. 60/239,281, "Measurement and Analysis of Cellular Response to Treatment in Asthma," filed Oct. 10, 2000; U.S. Provisional Application No. 60/246,137, "Effects of Oral Prednisone on Biological Markers of Asthma and Allergy," filed Nov. 6, 2000; and U.S. Provisional Application No. 60/304,563, "Effects of Oral Prednisone on Biological Markers of Asthma and Allergy," filed Jul. 10, 2001; all of which are herein incorporated by reference in their entirety.

FIELD OF THE INVENTION

The present invention relates generally to treatment of disease in humans and other mammals. More particularly, it relates to biological markers such as cell populations, cell surface antigen expression levels, and soluble factor concentrations that are indicative of the efficacy of treatment of atopic asthma and other inflammatory disorders.

BACKGROUND OF THE INVENTION

Prednisone is a corticosteroid used to treat a wide variety of inflammatory disorders, including asthma, atopy, arthritis, multiple sclerosis, ulcerative colitis, and Crohn's disease. While a comprehensive understanding of the action of prednisone and other glucocorticoids (a class of corticosteroids) is lacking, the drugs are known to have broad-ranging anti-inflammatory and immunosuppressive effects, including inhibition of pro-inflammatory mediators and activation of anti-inflammatory mediators. They affect the growth, differentiation, and function of monocytes and lymphocytes; the distribution of cellular subsets; and the production of cytokines, cellular proteins that are secreted and affect the behavior of other cells. Because the disorders treated by glucocorticoids themselves involve unknown immunological mechanisms, it is unclear which of the many effects of prednisone are most important in inhibiting the inflammatory response.

In addition, because of their broad-ranging systemic effects, prednisone and other glucocorticoids have a large number of side effects, some of them quite serious, which restrict their applicability in many patients, particularly for long-term use. These side effects include weight gain, hyperglycemia, bone thinning, digestive problems, cataracts, susceptibility to infection, hypertension, mood swings, and insomnia. It would be beneficial to have a drug that could provide the desired anti-inflammatory and immunosuppressive effects of prednisone without the detrimental side effects. Additionally, localizing the effects to the region of inflammation (e.g., the lungs) would minimize the systemic side effects. In order to do so, however, more information must be obtained about the mechanism of action of glucocorticoids in treating inflammatory disorders.

One very common inflammatory disease that has long been treated with prednisone is asthma, a chronic respiratory syndrome of uncertain etiology. Typical asthma symptoms include coughing, wheezing, chest tightness, and shortness of breath. These clinical symptoms are thought to result from hyper-responsiveness of the airways and a long-term inflammatory process that causes reversible obstruction of the airways. Many asthma sufferers also suffer from atopy, a hypersensitive allergic response to airborne antigens. The clinical manifestations of atopic asthma arise from the superposition of environmental factors on genetic predispositions that increase the probability of developing the syndrome.

Atopic asthma is an immunologic disease mediated by IgE antibodies and characterized by infiltration of the airways with mast cells, lymphocytes, and eosinophils.

The allergic response results from a hyperactivity of $T_H2$ (type 2 helper) T lymphocytes, triggering the production of cytokines such as interleukin (IL)-4, IL-5, IL-6, IL-10, and IL-13, which enhance antibody production from B cells and induce essential aspects of the allergic response, such as mucosal tissue injury by eosinophils. T cells also support IgE-mediated responses to airborne allergens and orchestrate the recruitment and activation of primary effector cells. Products released by the inflammatory cells accumulated in the airways contribute to the tissue destruction characteristic of asthma.

A large number of studies have been performed, mostly in vitro, to elucidate the anti-inflammatory mechanism of glucocorticoids in diseases such as asthma. One hypothesis is that glucocorticoids suppress the activation of cells that produce cytokines to prime eosinophils and induce the migration of lymphocytes, eosinophils, and basophils into the airway. Upon entering a cell, glucocorticoids bind with intracellular glucocorticoid receptors (GR), which are widely distributed among different cell types. The glucocorticoid-receptor complex then enters the cell nucleus and turns on specific genes by binding with DNA and directing the transcription process. In particular, glucocorticoids interact with two transcription factors, activating protein 1 (AP-1) and nuclear factor NF-κB. AP-1 is involved in the regulation of several genes, including those that express adhesion molecules and cytokines, while NF-κB regulates the transcription of genes involved in the inflammatory response. It is estimated that each cell type has ten or more target genes per cell, although they may not all be expressed. It would be highly desirable to develop new glucocorticoids or other drugs that would be more selective moderators of gene expression, leading to a reduction in toxic effects and localization of effects to disease regions.

Current studies on the effect of glucocorticoids on asthma and other inflammatory disorders are performed by measuring the effect of the drug on quantities of cell types, cell surface antigen expression, and soluble factors, both in vivo and in vitro. A number of factors have been shown to be correlated with glucocorticoid use, such as an increase in circulating granulocytes or decrease in number of eosinophils, which are responsible for many of the inflammatory tissue damage effects of asthma. However, while many studies examine IgE levels and related factors, there are few data available with respect to other measurements in vivo, such as cell surface marker expression on granulocytes and lymphocytes, or soluble factors in serum. Available data are also conflicting. For example, variable effects of glucocorticoids on T cell counts have been shown, while B cells are believed to be only minimally affected by glucocorticoids, with redistribution from peripheral blood to other lymphoid compartments being of main importance. There have also been conflicting reports on immunoglobulin levels post glucocorticoid treatment. As is well known to those of skill in the art, the correlation between in vitro and in vivo measurements is tenuous at best, and in vivo measurements must be performed to obtain information that can be used for treatment or diagnostic purposes.

Methods and compositions are currently being developed for alternative treatments of asthma and other inflammatory disorders that minimize side effects. Much of this work is devoted to regulation of the various interleukins. For example, U.S. Pat. No. 5,908,839, issued to Levitt et al., discloses methods for treating asthma by regulating the function of the IL-9 receptor. U.S. Pat. No. 5,683,983, issued to Barrett et al., discloses compounds that bind to the IL-5 receptor. U.S. Pat. No. 5,874,080, issued to Hebert et al., provides anti-IL-8 monoclonal antibodies for treatment of asthma.

In general, much more information must be obtained before less broad ranging but sufficiently effective anti-inflammatory drugs can be developed for treatment of autoimmune or inflammatory diseases such as asthma. In addition, accurate but simple methods for evaluating drug efficacy are lacking. One of the problems in elucidating both drug action and disease pathogenesis is that appropriate tools are lacking to measure a broad range of applicable immunological components in vivo from a large number of subjects. Thus many studies on the effects of glucocorticoids on cellular responses are performed in vitro or in animal models, neither of which is directly applicable to humans. In addition, the studies tend to examine factors that are already known to be implicated in glucocorticoid action, rather than searching for novel factors that may be useful for indicating the disease progression or treatment efficacy.

There is a need, therefore, for a simple but effective method of gauging the anti-inflammatory or immunosuppressive response of candidate drugs for treating asthma, atopy, and other inflammatory diseases. There is also a need for more information about the mechanism by which glucocorticoids inhibit the inflammatory response. Further, there is a need for methods to determine systemic versus local effects of administered drugs.

SUMMARY OF THE INVENTION

The present invention addresses these needs by providing novel biological markers (biomarkers) indicative of anti-inflammatory or immunosuppressive action of a drug in a subject. These novel biomarkers can be used to assess the anti-inflammatory action of a drug, detect systemic versus local effects of an anti-inflammatory drug, and better understand the mechanism of action of glucocorticoids such as prednisone. The information obtained can aid in selection of an appropriate glucocorticoid, dose, and administration route. Additionally, the information provided by the present invention can help in designing next generation drugs that have strong anti-inflammatory effects but fewer or less significant side effects than existing glucocorticoids.

The inventive biomarkers include cell populations, cell surface antigens, and soluble factors whose measurement values in a biological sample change significantly (either increase or decrease) after an anti-inflammatory drug is administered to the subject from whom the sample is obtained. In particular, these biomarkers include CD89 expression on granulocytes, CD38 expression on CD4 T cells, HLA class II expression on B cells, CD62L expression on B cells, monocyte count, HLA class II expression on monocytes, MMP-3 concentration, and SAA concentration.

In one embodiment, the invention provides a method for determining whether a candidate drug is effective in treating an inflammatory or autoimmune disease. Specific doses and delivery routes can also be examined. The method is performed by administering the candidate drug to a subject; obtaining a biological sample, such as a blood sample, from the subject; measuring the level of at least one of the inventive biological markers in the biological sample; and comparing the measured level with a standard level. Typically, the standard level is obtained by measuring the same marker or markers in the subject before drug administration. Depending upon the difference between the measured and standard levels, the drug can be considered to have an anti-inflammatory or immunosuppressive effect. Typical anti-inflammatory diseases treated by the candidate drug include atopy and asthma. If multiple biomarkers are measured, at least one and up to all of the biomarkers must change significantly, in the expected direction, for the drug to be considered anti-inflammatory. Preferably, multiple markers must change for the drug to be considered effective.

In an alternative embodiment, the present invention provides a method for detecting a systemic effect of an anti-inflammatory drug (e.g., a glucocorticoid such as prednisone) in a subject. In this method, a biological sample correlated with systemic activity, such as blood or urine, is obtained from the subject. Next, a set of factors including at least one of the inventive biomarkers is measured in the biological sample. The measured values are then compared with standard values, preferably measurements of the same biomarkers taken from the same subject before the drug was administered. Preferably, measurements are also made of a local biological sample, one correlated with local rather than systemic activity, extracted from the same subject. The change in local values after drug can be analyzed to determine whether the drug has local effects in addition to or instead of systemic effects.

DETAILED DESCRIPTION OF THE INVENTION

Figure 1A:
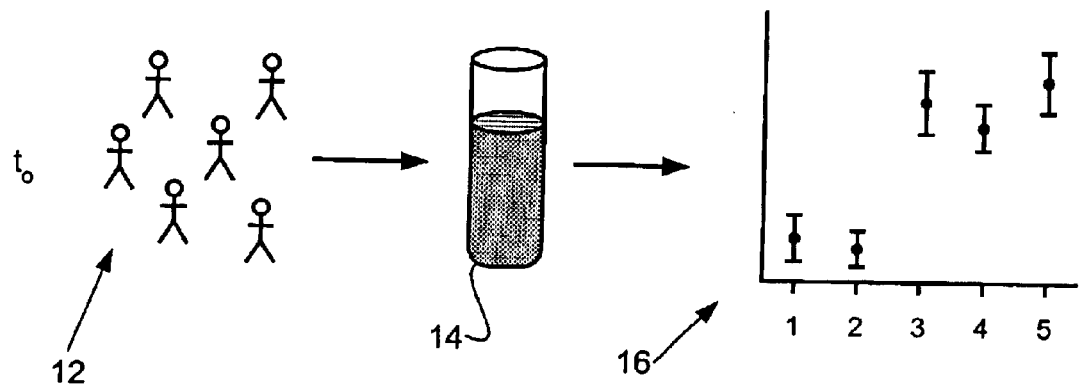
FIGS. 1A–1B are schematic diagrams illustrating a preferred embodiment of a method of the invention.

The present inventors have discovered novel biological markers whose presence and measurement levels are indicative of action of a drug, particularly a glucocorticoid, to inhibit inflammation or otherwise suppress the immune response in humans or other mammals. The inventive biomarkers include cell populations, cell surface antigen expression levels, and soluble factor concentrations. According to one definition (NIH), a biological marker (biomarker) is "a characteristic that is objectively measured and evaluated as an indicator of normal biologic processes, pathogenic processes, or pharmacological responses to therapeutic interventions." Biomarkers can also include patterns or ensembles of characteristics indicative of particular biological processes. Note that the biomarker measurement can increase or decrease to indicate a particular biological event or process. In addition, if the biomarker measurement typically changes in absence of the target event, a constant measurement value can indicate occurrence of the particular biological process. For more information on biomarker measurement and discovery, see U.S. application Ser. No. 09/558,909, "Phenotype and Biological Marker Identification System," filed 4/26/2000, herein incorporated by reference in its entirety.

A wide variety of biomarkers can be imagined, including those for diagnostic, therapeutic, prophylactic, drug discovery, and patient stratification purposes. In the present invention, the biomarkers are primarily indicative of a pharmacological response to a therapeutic intervention. They therefore can be considered to be efficacy biomarkers, a type of biomarker used to estimate the efficacy of a drug. In general, efficacy biomarkers must correlate with the clinical outcome (for example, reduced inflammation), be mechanistically linked to the disease progress, and significantly capture the treatment effect of the drug. The biomarkers of the present invention are believed to satisfy all of these criteria.

As described in further detail below, measurement values of the inventive biomarkers were found to change significantly after administration of oral prednisone to atopic asthmatics (allergic asthmatics), allergy sufferers, and healthy subjects, while no significant changes in their values were found in subjects taking a placebo. Because the administered dose of prednisone has been widely documented to inhibit inflammatory effects, it is believed that these markers are indicators of the anti-inflammatory action of glucocorticoids. Although the markers have not been predicted from existing knowledge of asthma pathogenesis and glucocorticoid action, they can be explained in the context of such knowledge.

The present invention includes all methods relying on correlations between the inventive biomarkers and anti-inflammatory or immunosuppressive actions of a drug. In a preferred embodiment, the invention provides methods for determining whether a candidate drug, particularly a glucocorticoid, is effective at treating an autoimmune or inflammatory disorder such as asthma or atopy. Different drugs, doses, and delivery routes can be considered by performing the method for different drug administration conditions of interest. In alternative embodiments, methods are provided for detecting systemic effects of anti-inflammatory drugs and comparing systemic and local effects. Additionally, methods are provided for designing drugs that target, supply, or stimulate production of the inventive biomarkers and are therefore effective at treating inflammatory or autoimmune disorders.

It is expected that the inventive biomarkers, described in detail below, will be measured in combination with known markers of glucocorticoid action. For example, C-reactive protein (CRP) is an acute-phase plasma protein that can increase 100- to 1000-fold after a subject's exposure to acute inflammatory stimuli, with serum levels typically peaking two or three days after stimulation. Intermediate levels (5- to 50-fold increase above normal) of CRP are associated with chronic inflammatory conditions such as cardiovascular disease. Glucocorticoids have been shown to decrease significantly the levels of CRP. Similarly, glucocorticoids have been shown to increase the total number of circulating granulocytes. They have also been shown to decrease expression of HLA-DP on monocytes. Of course, measurement of the inventive biomarkers along with any other markers known in the art, including those not specifically listed herein, falls within the scope of the present invention.

In one embodiment, the present invention provides a method for determining whether a candidate drug is effective in treating an inflammatory or autoimmune disease. An effective drug is one that provides a detectable change in the disease symptoms, such as a reduction in the amount of inflammation. For example, effectiveness in treating asthma can be gauged by measuring $FEV_1$ (forced expiratory volume in one second) with a flow meter before and after treatment. Inhibition of allergic response can be correlated with decreasing levels of the immunoglobulin IgE or an allergen-specific IgE in serum. Of course, there are ranges of drug efficacy in reducing inflammation or other disease symptoms, and any range of efficacy falls within the scope of the present invention. Methods of the present invention are used to determine whether a candidate drug is effective, independent of monitoring the disease symptoms themselves. Biomarker measurements are taken before and after drug administration, and significant changes in measurement values (in the correct direction) indicate anti-inflammatory action of the drug. Diseases and disorders whose treatments can be evaluated using the present method include atopy, asthma, and autoimmune diseases such as multiple sclerosis, Graves' disease, myasthenia gravis, rheumatoid arthritis, Crohn's disease, scleroderma, and acute rheumatic fever.

Figure 1B:
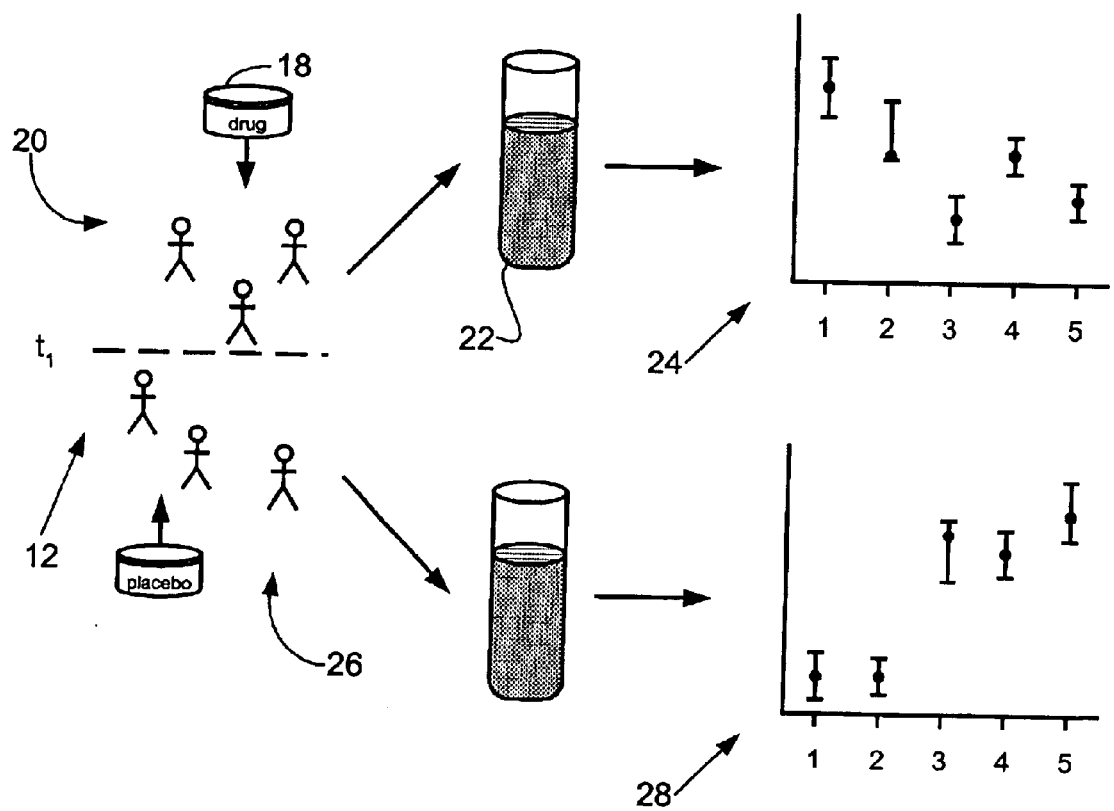

FIGS. 1A and 1B schematically illustrate this embodiment of the invention, a study of the effectiveness of a candidate anti-inflammatory drug. A subject population 12 having an inflammatory or autoimmune disorder such as asthma, atopy, or atopic asthma is selected for the study. The population 12 is typically selected using standard protocols for selecting clinical trial subjects. For example, the subjects are generally healthy, are not taking other medication, and are evenly distributed in age and sex. The subject population 12 can also be divided into multiple groups; for example, different sub-populations may be suffering from different disorders to which the candidate drug is addressed.

In general, a number of statistical considerations must be made in designing the study to ensure that statistically significant changes in biomarker measurements can be detected following drug administration. The amount of change in a biomarker depends upon a number of factors, including strength of the drug, dose of the drug, and treatment schedule. While larger changes are easier to detect, even small changes can be statistically significant and indicative of anti-inflammatory action of the drug. However, to be detected as significant, smaller changes require a larger subject population than do larger changes. In particular, the effect size of a measurement, the expected mean difference in measurements before and after drug divided by the standard deviation of the differences, determines the number of subjects that must be included in the study to observe significant differences. The number of subjects also depends upon the number of different independent biomarkers and the effect size being measured. For example, in order to observe a significant effect size of 1 or greater in measuring 5 uncorrelated variables, using a paired t-test, 22 subjects are needed. For detecting effect sizes of 0.5, 72 subjects are needed. It will be apparent to one skilled in statistics how to determine appropriate subject population sizes. Preferably, the study is designed to detect relatively small effect sizes. It is expected that newly developed drugs will be designed to have fewer and less severe side effects than currently available drugs, and therefore produce smaller overall changes at the cellular level.

The subjects are "washed out" from any previous drug use for a suitable period of time. Washout removes effects of any previous medications so that an accurate baseline measurement can be taken. At time $t_0$, a biological sample 14 is obtained from each subject in the population 12. Preferably, the sample is a blood sample, but other biological fluids may be used; for example, possible biological fluids include, but are not limited to, sputum, urine, bronchoalveolar lavage, bronchoalveolar wash, and nasal wash. Next, a variety of assays are performed on each subject's sample 14 to measure levels of particular cell populations, expressed cell surface antigens, and/or soluble factors. The assays can use conventional methods and reagents, as described below. If the sample is blood, then the assays are performed on either whole blood or on red blood cell-lysed blood. For other fluids, additional sample preparation steps are included as necessary before the assays are performed. The assays measure values of between one and all of the biological markers described below, and preferably all. In some embodiments, only a single factor is monitored, while in other embodiments, a combination of factors, up to the total number of factors, is monitored. The number of biological markers whose values are measured depends upon, for example, the availability of assay reagents, biological fluid, and other resources. Assay results are illustrated schematically in a chart 16, which contains the baseline measurement values.

Next, a predetermined dose of a candidate drug 18 is administered to a portion or sub-population 20 of the same subject population 12. Drug administration can follow any suitable schedule over any time period, and the sub-population 20 can include some or all of the subjects in the population 12. In some cases, varying doses are administered to different subjects within the sub-population 20, or the drug is administered by different routes (e.g., orally vs. inhaled). Suitable doses and administration routes depend upon specific characteristics of the drug. At time $t_1$, after drug administration, a biological sample 22 is acquired from the sub-population 20. Typically, the acquired sample is the same type of sample and processed in the same manner (for example, red blood cell-lysed) as the sample 14 acquired from the subject population 12 before drug administration. The same assays are performed on the biological sample 22 as on the biological sample 14 to obtain measurement values illustrated schematically in a chart 24. Subsequent sample acquisitions and measurements can be performed as many times as desired over a range of times $t_2$ to $t_n$.

Typically, a different sub-population of the subject population 12, a sub-population 26, is used as a control group, to which a placebo is administered. The same procedure is then followed for the control group 26: obtaining the biological sample, processing the sample, and measuring the biological markers to obtain a measurement chart 28. Additionally, different drugs can be administered to any number of different sub-populations to compare the effects of the multiple drugs. As will be apparent to those of ordinary skill in the art, the above description is a highly simplified description of a method involving a clinical trial. Clinical trials have many more procedural requirements, and it is to be understood that the method is typically implemented following all such requirements.

Paired measurements of the various biomarkers are now available for each subject. The different measurement values, represented by charts 16, 24, and 28, are compared and analyzed to determine whether the biological markers changed significantly in the expected direction for the drug group but not for the placebo group, indicating that the candidate drug is effective in treating the disease. The measurement values at time $t_1$ for the group that received the candidate drug are compared with standard measurement values, preferably the measured values before the drug was given to the group, i.e., at time $t_0$. Typically, the comparison takes the form of statistical analysis of the measured values of the entire population 20 before and after administration of the drug or placebo. Any conventional statistical method can be used to determine whether the changes in biological marker values are statistically significant. For example, paired comparisons can be made for each biomarker using either a parametric paired t-test or a non-parametric sign or sign rank test, depending upon the distribution of the data.

In addition, tests should be performed to ensure that statistically significant changes found in the drug group are not also found in the placebo group. Without such tests, it cannot be determined whether the observed changes occur in all patients and are therefore not a result of candidate drug administration. In essence, the slopes of the responses over time for both groups are compared, and only if the two groups do not behave similarly can the biomarker level changes in the drug group be attributed to the drug. One possible statistical technique to make this assessment is the repeated measures analysis of variance test. Other techniques, such as generalized linear models or linear mixed models, may also be employed. Note that a statistically significant difference between the slopes does not guarantee that the marker changed significantly in the candidate drug group; for this guarantee, the paired tests described above must be performed.

Preferably, the analysis also includes modifications to accommodate the performance of multiple tests on a single data set. Statistical tests of hypothesis validity are typically assessed by a p-value, the probability that a given outcome (or a more extreme one) could have occurred by chance alone. The p-value is computed assuming the null hypothesis to be true, i.e., that there is no significant difference between (in this case) the two paired points. If a p-value is found to be below the significance level $\alpha$, usually taken to be 0.05 in the univariate case, then the null hypothesis is rejected and the result considered to be statistically significant. A so-called type I error occurs when a true null hypothesis is rejected and a false positive result found. For this reason, $\alpha$ is often referred to as the false positive rate.

When multiple independent tests are made on the same dataset, as is the case with measuring multiple biomarkers, a distinction must be made between an individual test's false positive rate and the experiment-wise (overall) false positive rate. As the number of tests increases, the overall false positive rate quickly exceeds the desired rate. For the overall rate to remain at $\alpha$, the individual values used to assess the significance of each test's result must be lower than the overall rate. That is, the p-value for each biomarker's test must be significantly below 0.05 to maintain an overall false positive rate of 0.05. Preferably, the p-values are adjusted using the Bonferroni step-down down adjustment method of Holm, a conservative technique to control the false positive rate. The adjusted values, which are higher than the unadjusted values, incorporate the effect of performing multiple tests and can be compared individually to the overall $\alpha$. Biomarkers whose adjusted p-values are less than $\alpha$ have changed significantly after drug administration. Note that conservative statistics are most important when many variables are considered to obtain a complete pharmacodynamic profile of the administered drug. When fewer variables are measured, conservative statistics are less important.

As indicated below, some of the marker values increase with anti-inflammatory action, while others decrease. A significant change in the appropriate direction in the measured value of one or more of the markers indicates that the drug has an anti-inflammatory action. If only one biomarker is measured, then that value must increase or decrease to indicate drug efficacy. If more than one biomarker is measured, then drug efficacy can be indicated by change in only one biomarker, all biomarkers, or any number in between. Preferably, multiple markers are measured, and drug efficacy is indicated by changes in multiple markers. Measurements can be of both inventive biomarkers and known biomarkers (e.g., granulocyte counts). Furthermore, the amount of change in biomarker level may be an indication of the relative amount of inflammatory action or extent of a systemic effect.

In addition to determining whether a particular drug is effective in treating an inflammatory or autoimmune disorder, biomarkers of the invention can also be used to examine dose effects of a candidate drug. There are a number of different ways that varying doses can be examined. For example, different doses of a drug can be administered to different subject populations, and measurements corresponding to each dose analyzed to determine if the differences in the inventive biomarkers before and after drug administration are significant. In this way, a minimal dose required to effect a change can be estimated. In addition, results from different doses can be compared with each other to determine how each biomarker behaves as a function of dose.

Analogously, administration routes of a particular drug can be examined. The drug can be administered differently to different subject populations, and measurements corresponding to each administration route analyzed to determined if the differences in the inventive biomarkers before and after drug administration are significant. Results from the different routes can also be compared with each other directly. For example, a drug can be administered both orally and inhaled.

The present invention provides markers indicative of the action of an anti-inflammatory drug, specifically a glucocorticoid such as prednisone, in a subject. These biomarkers, monitored according to methods of the invention, have been shown by the present inventors to indicate the activity of an anti-inflammatory or immunosuppressive drug. The following inventive biomarkers are discussed in more detail below:

Increase in CD89 (FcαR) expression on granulocytes (both intensity of expression and percentage of granulocytes expressing CD89)

Decrease in CD38 expression on CD4 T cells

Decrease in HLA class II (DP, DR, DQ, PAN) expression on B cells

Decrease in CD62L (L-selectin) expression on B cells

Increase in monocyte count

Decrease in HLA class II (DP, DQ, PAN) expression on monocytes (both intensity of expression and percentage of monocytes expressing HLA class II antigens)

Increase in MMP-3 (stromelysin) concentration

Increase in serum amyloid A (SAA) concentration

To the knowledge of the present inventors, these markers have never before been shown or predicted to be biomarkers for anti-inflammatory drug efficacy. In particular, there are no previous results indicating a correlation between these observations and prednisone or other glucocorticoids in vivo. It is to be understood that any correlations between in vivo biological sample measurements of these biomarkers and anti-inflammatory action, as used for evaluating drug presence or efficacy or designing therapies, are within the scope of the present invention.

In methods of the invention, biomarker levels are measured using conventional techniques. Cellular assays measure levels of granulocytes, T cells, B cells, and monocytes and are preferably performed by flow cytometry or microvolume laser scanning cytometry, which allows absolute cell counts to be obtained. Cells are labeled with commercially-available antibody reagents and analyzed by cytometry. For measuring the inventive biological markers, cytometry measurements are required of granulocyte count, CD89 expression on granulocytes, CD4 T cell count, CD38 expression on CD4 T cells, monocyte count, HLA class II expression on monocytes, B cell count, and HLA class II and CD62L expression on B cells.

Granulocytes are identified using antibodies for the cell surface molecules CD15 and CD16. Within the granulocyte population, CD89 expression is quantified using antibodies for CD89. Both the relative number of granulocytes expressing CD89 and the intensity of expression of CD89 can be counted. CD4 T cells are identified using antibodies to CD4. CD38 expression on CD4 T cells is quantified using antibodies to CD38. Monocytes are identified using CD14 monoclonal antibodies, and B cells are identified using CD20 antibodies. Finally, HLA class II antigens are quantified using antibodies to HLA-PAN, HLA-DR, and HLA-DQ; and CD62L is identified using antibodies to CD62L.

MMP-3 and SAA concentrations are preferably measured by sandwiched ELISA using matched antibody pairs and chemiluminescent detection. Commercially available monoclonal or polyclonal antibodies can be used. Standard protocols and data analysis are used to determine the soluble factor concentrations from the assay data.

CD89 Expression on Granulocytes.

Granulocytes, which include neutrophils, eosinophils, and basophils, include both phagocytic cells and cells that release toxic and mediating compounds. In the present invention, a statistically significant increase in CD89 expression by granulocytes following administration of the candidate drug indicates that the drug has an anti-inflammatory or immunosuppressive effect. As mentioned above, CD89 expression is reported in two different ways, both of which are indicative of an anti-inflammatory action. First, anti-inflammatory drugs are correlated with an increase in the relative percentage of granulocytes that express CD89. Second, an increase in intensity of expression of CD89 on granulocytes indicates anti-inflammatory action of the drug.

CD89 (FcαR) is the Fc receptor for the antibody IgA and is capable of binding monomeric, dimeric, and polymeric IgA. IgA is the predominant imunoglobulin in the mucosal surfaces of the respiratory tract, where it can eliminate excess antigens without inducing potentially harmful inflammatory reactions. In addition to its antibody activity, IgA is known to have an independent regulatory activity upon interaction with CD89 on monocytes and neutrophils. In monocytes, binding of IgA with CD89 has been shown to down-regulate production of the inflammatory cytokines TNFα and IL-6 and to induce IL-1 receptor antagonist (IL-IRa), an inhibitor of pro-inflammatory IL-1 activity (H. M. Wolf et al., "Anti-inflammatory properties of human serum IgA: induction of IL-1 receptor antagonist and FcαR (CD89)-mediated down-regulation of tumour necrosis factor-alpha (TNF-α) and IL-6 in human monocytes," Clin. Exp. Immunol., 105: 537–543 (1996)). It is believed that the increased CD89 expression on granulocytes has a similar regulatory effect.

CD38 Expression on CD4 T Cells.

CD4 T lymphocytes, which include helper and inflammatory T cells, activate macrophages and B cells. According to the present invention, anti-inflammatory drugs decrease CD38+ CD4 T cells as a percentage of total CD4 T cells. Depending on the cellular environment, CD38 can be either a positive or a negative regulator of cell activation and proliferation. It has also been shown to be involved in adhesion between human lymphocytes and endothelial cells (S. Read et al., "CD38+ CD45RB$^{low}$ CD4+ T cells: a population of T cells with immune regulatory activities in vitro," Eur. J. Imunol., 28: 3435–3447 (1998)). In vitro corticosteroid treatment has been shown to affect CD38$^+$ T cells (S. Vukmanovic et al., "An Unusual T-Cell Surface Phenotype in Vivo Correlates with the Failure to Proliferate and Produce IL-2 in Vitro in a Patient with Common Variable Immunodeficiency," *Clin. Immunol. Immunopathol.,* 65: 261–270 (1992)), but there has previously been no evidence of its correlation with corticosteroids in vivo.

HLA Class II Expression on B cells.

B cells whose receptors have recognized an antigen express HLA class II molecules bound to fragments of the degraded antigen. Helper CD4 T cells recognize the complex of antigenic fragment and HLA molecule and activate the B cell to proliferate and produce antibody. In the present invention, anti-inflammatory action of the candidate drug is correlated with a decrease in HLA class II expression. Specifically, DP, DR, DQ, and PAN expression all decrease. This decrease indicates a less activated state after drug administration and may reflect a diminished capacity for B cells to act as antigen presenting cells. Although a decrease in HLA class II expression on CD4 T cells (V. Gemou-Engesaeth et al., "Inhaled Glucocorticoid Therapy of Childhood Asthma Is Associated With Reduced Peripheral Blood T Cell Activation and 'Th2-Type' Cytokine mRNA Expression," *Pediatrics,* 99: 695–703 (1997)) and on monocytes (A. G. Oehling et al., "Suppression of the immune system by oral glucocorticoid therapy in bronchial asthma," *Allergy,* 52: 144–154 (1997)) has been shown after prednisone treatment, the effect has not previously been shown on B cells.

CD62L (L-selectin) Expression on B cells.

L-selectin is part of the selectin family of adhesion molecules, which mediate the initial attachment of cells to venular epithelial cells at sites of tissue injury and inflammation. Selectin-directed therapeutic agents are effective in blocking many pathological effects resulting from leukocyte entry into inflammation sites (T. F. Tedder at al., "The selecting: vascular adhesion molecules," *FASEB J,* 9: 866–873 (1995)). According to the present invention, a decrease in CD62L expression on B cells is correlated with anti-inflammatory action of the candidate drug.

Monocytes.

Monocytes are antigen-presenting cells that play a key role in the inflammatory response. They release a variety of mediators including complement proteins; IL-1, IL-6, and TNFα; growth-promoting molecules such as platelet derived growth factor and TGF-β; small lipid derivatives such as arachidonate; and enzymes that affect connective tissue and serum proteins such as collagenase. In the present invention, a statistically significant increase in circulating monocyte count following administration of the candidate drug indicates that the drug has an anti-inflammatory or immunosuppressive effect. This is in direct contrast to teachings in the prior art, in which monocytes were found to decrease in response to glucocorticoid therapy (A. S. Fauci et al., "The effect of in vivo hydrocortisone on subpopulations of human lymphocytes," *J. Clin. Invest.,* 53: 240–246 (1974)).

HLA class II Expression on Monocytes.

In the present invention, anti-inflammatory action of the candidate drug is correlated with a decrease in HLA class II expression on monocytes, both intensity of expression and the percentage of monocytes expressing HLA class II antigens. Specifically, DP, DR, DQ, and PAN expression all decrease. As with B cells, this decrease indicates a less activated state after drug administration and may reflect a diminished capacity for monocytes to act as antigen presenting cells.

MMP-3.

The matrix metalloproteinases (MMPs) are members of a family of proteolytic enzymes that are capable of degrading a range of extracellular matrix proteins. MMP-3 (stromelysin) has been implicated in the release of growth factors that enhance airway fibrosis (abnormal spread of fiberlike connective tissue), a structural contributor to airway wall thickening. These structural changes have also been correlated with progressive decline in lung function. MMP-3 co-localizes to mast cells, eosinophils, and neutrophils in bronchial tissue.

In the present invention, an increase in MMP-3 concentration indicates an anti-inflammatory action of the administered candidate drug. In previous studies, MMP-3 concentration was shown to reflect rheumatoid arthritis activity; that is, an increase in MMP-3 indicated more inflammatory action. In osteoarthritis studies, glucocorticoids have been shown to suppress MMP synthesis (DiBattista et al., "Glucocorticoid Receptor Mediated Inhibition of Interleukin-1 Stimulated Neutral Metalloprotease Synthesis in Normal Human Chondrocytes," *J. Clin. EndocrinoL Metab.,* 72: 316–326 (1991)), in contrast to the increase found in the present invention.

SAA.

Serum amyloid A (SAA) is an acute-phase plasma protein whose concentration can increase 10- to 1000-fold after exposure to acute inflammatory stimuli. Serum levels typically peak two or three days after stimulation. In the present invention, an increase in SAA concentration indicates an anti-inflammatory action of the administered candidate drug. In previous clinical and in vivo studies in animals, SAA concentration was shown to decrease with corticosteroids (Marhaug et al., "Serum amyloid A: an acute phase apolipoprotein and precursor of AA amyloid," *Baillieres Clin. Rheumatol.,* 8: 553–572 (1994). However, in most in vitro studies, corticosteroids increase SAA production in cultured cells (Jensen et al., "Regulation of serum amyloid A protein expression during the acute-phase response," *Biochem J.,* 334: 489–503 (1998)). In vitro, the dramatic induction of SAA mRNA in response to pro-inflammatory stimuli is due largely to the synergistic effects of cytokine signaling pathways, principally those of IL-1 and IL-6; this induction can be enhanced by glucocorticoids. Note that CRP, as mentioned above, has previously been shown to decrease in response to glucocorticoids, in contrast to SAA. It is advantageous to measure both soluble factors to gain more information about the effect of the candidate drug.

One desired quality of an anti-inflammatory drug is that its effect is local, rather than systemic. A local action addresses the disease symptoms and directly affects the disease pathway without causing broad-ranging side effects. Oral corticosteroids are known to have a very large systemic effect, and therefore decrease the disease symptoms while also producing side effects localized to other regions of the body. Systemic effects can be detected in biological fluids such as blood and urine. Local effects, in contrast, can be detected only minimally, if at all, in the blood, but can be detected in localized fluids such as sputum, bronchoalveolar wash, and bronchoalveolar lavage. Note that identifying a systemic effect of a drug can be desirable or undesirable, depending upon the context. Because a drug that affects the entire system also affects the local region of inflammation, the detected systemic effect indicates that drug has the desired anti-inflammatory or immunosuppressive action. However, if the systemic effect includes undesirable side effects, then it is desirable to minimize the systemic effect while maximizing the local effect. The present invention can be used to evaluate the type of effect a drug is causing.

In an alternative embodiment of the invention, a method is provided for detecting whether a systemic effect has been produced by an anti-inflammatory drug, particularly a glucocorticoid such as prednisone. The specific techniques used in implementing this embodiment are similar to those used in the embodiment described above. Again, a subject population is chosen as described above and washed out from all previous drug use. A baseline measurement is obtained by acquiring a biological sample indicative of systemic effects, such as blood or urine, from each subject. The samples are then analyzed using the assays described above to measure the inventive biomarkers or some number of the inventive biomarkers. Subsequently, a suitable treatment regimen of the anti-inflammatory drug is administered to a portion of the subjects, and the same type of sample is acquired from the subject group at some time after drug administration. Measurements are again made of the inventive biomarkers, or some portion of the inventive biomarkers. The measurements before and after are compared, preferably using the statistical analyses described above, to determine whether statistically significant differences in the biomarker values are found before and after drug administration. If the values of at least some (and preferably all) of the biomarkers are found to be different, and if the differences are in the correct direction, then it is likely that the administered drug has a systemic effect.

This embodiment of the invention can be particularly useful for testing whether a drug believed to have only a local effect, or a method of delivery believed to have only a local effect, actually has a systemic effect. Furthermore, the measured values of the biomarkers can be indicative of the degree of the effect. That is, for a given dose and type of drug, a larger change in biomarker can, in some cases, be correlated with a larger systemic effect. The amount of change in biomarker value can also be correlated with the administered dose of the drug.

In a further additional embodiment, comparisons can be made between local and systemic effects by measuring the same biomarkers in fluids that are more representative of local action, rather than systemic action. Such fluids include sputum, nasal wash, bronchoalveolar lavage, and bronchoalveolar wash. In this embodiment, different biological fluids are obtained from the subjects at a single time point. The obtained fluids include both a fluid indicative of local effects and a fluid indicative of systemic effects. Measurements are made before and after drug administration as described above for the previous embodiments. Similar analysis is made of the different fluids as described above for single fluids. The amount of change in biomarker values before and after drug administration is compared for the different fluids. If, for example, no significant changes are seen in blood, while large changes are seen in sputum, there is an indication that the drug or delivery method has predominantly local effects. Alternatively, if statistically significant changes are noted in both fluids, then it is likely that the drug has both local and systemic effects.

Different fluids require different sample collection and preparation methods. For example, sputum, bronchoalveoar wash, and bronchoalveolar lavage are preferably collected by the following methods. Sputum induction is accomplished after methacholine challenge. Subjects are pretreated with 360 $\mu$g albuterol administered by metered dose inhaler (4 puffs) with repeat spirometry 10 minutes later to document that the post-albuterol $FEV_1$ is $\geq 60\%$ predicted. Subjects are then seated in an aerosol containment chamber where they inhale nebulized sterile 3 % saline for 12 minutes using a mouthpiece connected by corrugated tubing to an ultrasonic nebulizer. The procedure is interrupted every 2 minutes to allow for expectoration and subjects are instructed to spit into a plastic container before coughing deeply into a separate sterile plastic container for analysis. In all subjects, PEF is monitored at 2-minute intervals and those whose PEF declined to $\leq 80\%$ of baseline post-bronchodilator $FEV_1$ will have the induction stopped. Sputum samples are incubated with DTT, DNAse and collagenase, washed, centrifuged and counted to yield a single cell suspension free of mucosal fluid. Staining for airway secretions is best performed done on ice, with washing to reduce non-specific staining.

Bronchoscopy, by which broncheoalveolar fluids are obtained, involves passing a flexible bronchoscope through the mouth and into the lungs. Subjects fast for 8 hours before bronchoscopy. Subjects are given an injection of atropine to reduce bronchial secretions. Subjects may also receive morphine, fentanyl or midazolam, if needed, to suppress cough or to reduce anxiety. Morphine and fentanyl are given to suppress cough. Midazolam is a drug like diazepam and is given to reduce gagging and nervousness. Atropine and morphine, if given, are given intramuscularly or intravenously while midazolam, if given, is given intravenously. Mouth and throat are anesthetized by spraying lidocaine, a bitter-tasting anesthetic, and cotton soaked in lidocaine is touched to the back of the throat. The bronchoscope, which is about the thickness of a pencil (¼ inch), is passed through the mouth and between vocal cords, after which time the subject is unable to talk. Small amounts of lidocaine are sprayed through the bronchoscope onto the vocal cords and other areas within the lung to abolish cough. The bronchoscope is passed into one of the bronchial tubes on the right lung and 50 ml (2 ounces) of saline infused and immediately removed by suction through the suction channel of the bronchoscope (bronchial washing). Then the bronchoscope is wedged in the distal airway and 2 more samples of 50 ml of saline are infused and immediately removed by suction as well (bronchioalveolar lavage). The bronchoscope is in place for 10–15 minutes. During the procedure, the subject has continuous pulse oximetry monitoring and frequent measurement of blood pressure, respiratory rate and pulse rate. After bronchoscopy, subjects are monitored for 2 hours until they recover the gagging reflex and are able to eat and drink. Bronchial samples are centrifuged, counted and resuspended at standard concentration for staining.

Note that while statistically significant effects can only be detected in the context of a suitable sample size, trends can be noted in single subjects or in a very small subject population. For example, the inventive biological markers can be measured in a single person before and after administration of a drug. If the change in biomarker value is consistent with the change expected for a large subject population taking an anti-inflammatory drug, then the result may provide encouragement for proceeding with a larger study.

As described below, the inventive biomarkers were discovered during a study of prednisone on atopic and asthmatic subjects. Thus it is expected that a large number of the inventive biomarkers are relevant for anti-inflammatory drugs having a structure similar to that of prednisone. As the drug structure becomes increasingly different from that of prednisone, however, it is likely that only a subset of the inventive biomarkers will change as expected. Furthermore, it is likely that the amount of change in biomarker value caused by the candidate drugs will be less than the amount caused by prednisone.

Prednisone is a glucocorticoid, a class of corticosteroids, compounds with the general ring structure of steroids. Other glucocorticoids include dexamethasone, cortisol, cortisone, triamcinolone acetonide, betamethasone, prednisolone, and methylprednisolone. Briefly, glucocorticoids induce numerous cellular and physiological effects that are mediated predominantly through their interaction with the cytosolic steroid hormone receptor GR (glucocorticoid receptor). Glucocorticoid enters the cell and binds with the GR. The glucocorticoid-receptor complex then enters the cell nucleus and turns on specific genes by binding with DNA and directing the transcription process. Because this mechanism is specific to glucocorticoids, it is believed that fewer of the inventive biomarkers will be relevant to anti-inflammatory drugs having significantly different structures.

In fact, as additional candidate drugs are tested using methods of the invention, it will be possible to determine which of the biomarkers are correlated with desired effects and which are correlated with side effects or less desired effects. This information can then be used in designing and developing drugs tailored to address only relevant disease mechanisms while causing fewer side effects.

In this additional embodiment of the invention, different candidate drugs are administered to subjects, and the side effects and anti-inflammatory or immunosuppressive actions documented. Any conventional metrics of anti-inflammatory action and side effect severity can be used. In addition, before and after drug administration, the inventive biomarkers are measured, either with or without additional markers or factors. Measurement levels are analyzed to determine which biomarkers change significantly. In this way, the biomarkers affected by each drug can be correlated with the particular desirable and undesirable effects of the drug. It is anticipated that new drugs being developed will have fewer side effects and cause changes in fewer of the inventive biomarkers. As additional generations of drugs are developed, the list of relevant biomarkers and their amount of change can be refined further. In addition, as it becomes clear whether each biomarker is indicative of desired or undesired effects, more information about the mechanisms of drug action are learned, helping to direct development of next generation drugs.

Although the invention has been described in the context of administering anti-inflammatory drugs to humans, it can be equally well applied to detecting the effects of anti-inflammatory drugs in animal models, particularly those with immune systems similar to the human immune system. For example, suitable animals include mice, rats, and rabbits.

The novel biomarkers of the present invention can also be used to help in designing anti-inflammatory or immunosuppressive drugs with fewer and less severe side effects than those of prednisone. For example, treatment can be developed to increase MMP-3 expression or CD89 expression on granulocytes.

The present invention represents a specific practical application of a general biomarker discovery method described in U.S. application Ser. No. 09/558,909, "Phenotype and Biological Marker Identification System," filed Apr. 26, 2000, herein incorporated by reference in its entirety. In this particular case, the method was used to phenotype asthma and allergy patients before and after administration of the glucocorticoid prednisone and a placebo. This technique allows rapid, efficient, and accurate measurement of a broad range of cell populations, cell surface antigen expression levels, and soluble factors. Because the phenotyping system can measure such a large number of variables, it facilitates discovery of novel biomarkers. Without such a tool, studies focus predominantly on factors already known or believed to be important in disease pathogenesis or drug behavior. Although the example was used to obtain a complete pharmacodynamic profile of drug action, the present invention is focused primarily on the novel biomarkers discovered within the profile.

The following example describes measurement, analysis, and identification of the inventive biomarkers.

EXAMPLE

Effect of Prednisone on Biological Markers of Atopy and Asthma

Methods

The inventive biomarkers were identified in a study of the effects of oral prednisone on biological markers of allergy and asthma. Eighty subjects were enrolled in the study, 23 with atopic asthma, 28 with allergy alone, 26 with neither allergy nor asthma (healthy controls), and 3 with asthma alone. Allergy was defined by a positive skin prick test. Mild asthma was defined as positive methacholine challenge within the last three months, as well as one or more of documented diagnosis of asthma, history of cough, recurrent wheeze, recurrent difficult breathing, and recurrent chest tightening. Approximately half of the subjects from each disease group were given oral prednisone for three days, while the other half was given a placebo. Blood samples were taken before treatment and after three days of treatment with oral prednisone or placebo.

Cellular markers in the blood samples were evaluated using the SurroScan™ microvolume laser scanning cytometry system for multiparameter cellular analysis. Monoclonal antigen-specific antibodies were purchased from commercial vendors and coupled to one of three different fluorophores, Cy5, Cy5.5, and Cy7-APC. Assays were performed to monitor cell counts of more than 200 different cell populations, including granulocytes, eosinophils, monocytes, CD4 and CD8 T cells, B cells, and NK cells. In addition, the relative levels of 49 different cell surface antigens (activation antigens, co-stimulatory molecules, adhesion molecules, antigen receptors, cytokine receptors) on specific cell populations were measured. The prepared antibody-dye reagents were combined into cocktails and incubated with aliquots of whole or red blood cell-lysed blood in the dark at room temperature for 20 minutes. The samples were then diluted with an appropriate buffer and loaded into capillary arrays for analysis. Each fluorophore was measured in a separate detection channel, and images were converted to flow cytometry standard format and analyzed with FlowJO™ cytometry analysis software. Template gates were used to enumerate the cell populations of interest in all of the assays.

Soluble factor assays were in a sandwich ELISA format using matched antibody pairs and chemiluminescent detection. Sixty-seven soluble factor assays were performed using commercially-available monoclonal and polyclonal analyte-specific antibodies. Capture antibodies were incubated in 96-well black opaque microtiter plates overnight at 4° C., washed, and blocked. Samples were added to the wells, incubated, and washed. Biotinylated detection antibody was then added, incubated, and washed, followed by incubation with avidin-alkaline phosphatase and another wash. Finally, the chemiluminescent alkaline phosphatase substrate was added and incubated before reading. Standard curves and analyte amounts were determined using curve fitting techniques.

Data Analysis

Following data acquisition, variables were analyzed to assess differences in subject groups before drug administration, as well as changes following drug administration. A total of 713 variables, including cell populations, cell surface antigen expression, and soluble factors, were analyzed. Because this data set contains more variables than subjects, and because all variables were considered potential biomarkers, many statistical techniques were not applicable, and a more conservative approach was used to analyze the data. Univariate tests were performed on individual variables, and the step-down Bonferroni p-value adjustment method of Holm was employed to control for multiple comparisons. The Bonferroni correction, which reduces the number of false positives, is described above.

The drug and placebo samples before drug administration were analyzed using the nonparametric Wilcoxon two-sample test and a parametric two-sample t-test. All of the p-values were adjusted using the step-down Bonferroni method. The different disease groups (allergy, asthma-allergy, healthy) were compared using the nonparametric Kruskal-Wallis test and analysis of variables (ANOVA) techniques, with p-values adjusted by the step-down Bonferroni method.

Univariate tests were performed on the data before and after drug administration for both the drug and placebo groups. In order to determine whether any non-normality of the data affected the tests, both non-parametric tests (sign rank or sign) and parametric paired t-tests were performed. Statistical tests for normality, skewness, and kurtosis were performed per variable to assess normality. For sufficiently normally distributed data, the paired t-test result was used; otherwise, the nonparametric result was used. All p-values were adjusted using the step-down Bonferroni method, maintaining the overall study false positive rate below 5%. 27% of the variables showed significant differences before and after drug administration. When the analysis was performed on the separate disease classes individually, no significant differences were found before and after drug administration.

Additionally, a linear-mixed model was used to evaluate fixed and random effects for the prednisone and placebo groups. This model notes the difference in response in the drug and placebo to indicate whether the observed trends can be attributed to the drug alone. The model, executed with PROC MIXED in SAS™, used the three fixed effects of drug, time, and (drug×time) to fit the data. All of the inventive biomarkers found to change significantly with the paired tests were also found to be significant with the linear mixed model.

Finally, one and two variable discriminant analyses were performed to differentiate the prednisone and placebo groups. Discriminant analysis determines which variables can be used to classify subjects into groups. Normalized variables (difference over time divided by initial value) were calculated from the raw data to create better discriminators. All of the variables were analyzed in the single variable discriminant analysis, and variables shown to be significantly different between the two groups were included in the two variable discriminant analysis. Good discriminators were selected based on two criteria: a low classification error rate and a low number of missing values.

Results

The two subject groups, prednisone and placebo, were found to be statistically equivalent. There was only one significant difference, based on the adjusted p-value, among the three different disease groups before treatment. As expected, the asthma-allergy and allergy-only groups had significantly higher (adjusted p-value<0.007) serum IgE levels than the healthy group before treatment.

Table 1 shows mean values before and after drug administration for the inventive biomarkers. Standard deviations are shown in parentheses. The results are for all disease groups, atopic, atopic asthmatic, and healthy subjects. Results for other measured variables are not shown. Tests for all biomarkers had an adjusted p-value of less than 0.001. Cell surface expression intensity levels are in arbitrary units.

TABLE 1

| Population/Antigen/Analyte | Mean Pre Drug (SD) | Mean Post Drug (SD) |
|---|---|---|
| CD89$^+$ granulocyte population (% of total granulocytes) | 85 (20) | 96 (9) |
| CD89 on granulocytes | 2047 (1549) | 2527 (1691) |
| CD38$^+$ CD4 T cells (% of all CD4 T cells) | 32.9 (9.8) | 29.3 (9.1) |
| HLA-DQ on B cells | 3123 (1090) | 1680 (817) |
| HLA-DR on B cells | 8108 (2711) | 4486 (2025) |
| HLA-PAN on B cells | 11684 (3190) | 6550 (3123) |
| CD62L on B cells | 2998 (505) | 2479 (478) |
| Monocytes (cells/μl) | 369 (121) | 478 (160) |
| HLADQ$^+$ monocyte population (% of total monocytes) | 8.7 (4.39) | 3.6 (2.49) |
| HLADR$^+$ monocyte population (% of total monocytes) | 84.4 (14.0) | 75.4 (16.9) |
| HLAPAN$^+$ monocyte population (% of total monocytes) | 91.8 (8.4) | 83.0 (15.1) |
| HLA-DQ on monocytes | 165 (103) | 69 (52) |
| HLA-DR on monocytes | 2966 (1068) | 1970 (729) |
| HLA-PAN on monocytes | 4961 (1738) | 3196 (1046) |
| MMP-3 (ng/ml) | 37 (29) | 188 (140) |
| SAA (μg/ml) | 2.73 (3.3) | 6.71 (14.5) |

Note that HLA-DP expression on monocytes and B cells was not measured. However, it is expected that the HLA-DP response to glucocorticoids is similar to that of the other HLA class II antigens.

The discriminant analysis showed HLA class II expression on B cells to be one of the best discriminators between prednisone and placebo. HLA-PAN misclassified only 3 subjects, while HLA-DQ and HLA-DR misclassified only 4 subjects. These three subjects were in the prednisone group but were misclassified into the placebo group. Based on other information, the misclassified subjects are believed not to have complied with the study protocol.

Note also that although only asthma and allergy were studied, the effects were noted in all subjects, even the healthy controls. Thus the anti-inflammatory and immuno-suppressive effects are not specific to treatment of asthma or atopy, but to any disorder being treated by glucocorticoids.

It should be noted that the foregoing description is only illustrative of the invention. Various alternatives and modifications can be devised by those skilled in the art without departing from the invention. Accordingly, the present invention is intended to embrace all such alternatives, modifications and variances which fall within the scope of the disclosed invention.

What is claimed is:

1. A method for determining whether a glucocorticoid drug is effective in treating a atopy or asthma, comprising:
   administering said candidate drug to a subject;
   obtaining a biological sample from said subject;
   measuring values of a set of factors in said sample, wherein said set of factors comprises at least two factors selected from the group consisting of:
      CD89 expression on granulocytes,
      CD38 expression on CD4 T cells,
      HLA-DP, HLA-DQ, HLA-DR, and HLA-PAN expression on B cells,
      CD62L expression on B cells,
      monocyte count, HLA-DP, HLA-DQ, HLA-DR, and HLA-PAN expression on monocytes, MMP-3 concentration, and SAA concentration; and comparing said measured values with standard values.

2. The method of claim 1, wherein said set of factors comprises at least three factors selected from said group.

3. The method of claim 1, wherein said standard values are obtained by measuring values of said set of factors in an additional sample acquired from said subject before said candidate drug is administered.

4. The method of claim 1, further comprising determining whether said glucocorticoid drug is effective in treating atopy or asthma in dependence on said comparison.

5. The method of claim 1, wherein a particular dose of said glucocorticoid drug is administered, and wherein the method further comprises determining whether said particular dose is effective in treating atopy or asthma in dependence on said comparison.

6. The method of claim 1, wherein said glucocorticoid drug is administered by a particular delivery route, and wherein the method further comprises determining whether said particular delivery route is effective in treating atopy or asthma in dependence on said comparison.

7. The method of claim 1, wherein said atopy or asthma is atopy asthma.

8. The method of claim 1, wherein said biological sample is a blood sample.

9. The method of claim 1, further comprising measuring values of at least one of granulocyte count and CRP concentration.

10. A method for detecting a systemic effect of a glucocorticoid drug in a subject, comprising:

obtaining a biological sample from said subject, wherein said sample is correlated with systemic activity;

measuring values of a set of factors in said sample, wherein said set comprises at least one factor selected from the group consisting of:

CD89 expression on granulocytes,

CD38 expression on CD4 T cells,

HLA-DP, HLA-DQ, HLA-DR, and HLA-PAN expression on B cells,

CD62L expression on B cells, monocyte count,

HLA-DP, HLA-DQ, HLA-DR, and HLA-PAN expression on monocytes,

MMP-3 concentration, and

SAA concentration; and comparing said measured values with standard values.

11. The method of claim 10, wherein said glucocorticoid drug is prednisone.

12. The method of claim 10, wherein said biological sample is selected from the group consisting of blood and urine.

13. The method of claim 10, further comprising obtaining a local biological sample from said subject, wherein said local biological sample is correlated with local activity, and measuring local values in said local biological sample.

* * * * *